(12) United States Patent
Ein-Gal

(10) Patent No.: US 7,688,939 B2
(45) Date of Patent: Mar. 30, 2010

(54) OBJECT ROTATION FOR CT DATA ACQUISITION

(76) Inventor: Moshe Ein-Gal, 30 Azar Street, Ramat Hasharon 47203 (IL)

(*) Notice: Subject to any disclaimer, the term of this patent is extended or adjusted under 35 U.S.C. 154(b) by 0 days.

(21) Appl. No.: 11/926,145

(22) Filed: Oct. 29, 2007

(65) Prior Publication Data

US 2009/0110142 A1    Apr. 30, 2009

(51) Int. Cl.
*A61B 6/00*    (2006.01)
(52) U.S. Cl. .............................. 378/20; 378/4
(58) Field of Classification Search ............. 378/4, 378/15, 17, 19, 20, 62, 208
See application file for complete search history.

(56) References Cited

U.S. PATENT DOCUMENTS

| | | | |
|---|---|---|---|
| 7,170,966 B2 * | 1/2007 | Kuo-Petravic et al. | 378/4 |
| 7,388,941 B2 * | 6/2008 | Sukovic et al. | 378/19 |
| 2002/0097831 A1 * | 7/2002 | Cheng | 378/20 |
| 2005/0226370 A1 * | 10/2005 | Al-khalidy et al. | 378/27 |

* cited by examiner

*Primary Examiner*—Irakli Kiknadze
(74) *Attorney, Agent, or Firm*—Dekel Patent Ltd; David Klein

(57) ABSTRACT

A computed tomography (CT) scanning system including a source operable to emit a cone beam of radiation toward an object, a detector operable to detect radiation emitted by the source and to produce detector values related to projections of an object attenuation, a turntable operable to rotate the object about a rotational axis, and a source mover operable to move the source so as to vary an angle between the cone beam and the rotational axis.

9 Claims, 2 Drawing Sheets

OBJECT ROTATION FOR CT DATA ACQUISITION

FIELD OF THE INVENTION

The present invention relates generally to rotating-patient computed tomography (CT) scanning devices and techniques, and particularly to improved source trajectories therefor.

BACKGROUND OF THE INVENTION

CT scanning typically involves a radiation source and a matching detector rotating about a recumbent patient. In such so-called "rotating patient" computed tomography (CT) scanners, the patient is positioned in an upright position between an x-ray source and a bank of x-ray detectors, the source and detectors being fixed relative to one another. The patient is rotated through small incremental angles about a vertical rotation axis as x-rays are passed from the source through the patient to the detectors. For any given focal spot and detector position, a view or projection is obtained which provides data about a given two-dimensional slice of the patient's anatomy within a horizontal scan plane. The patient is then rotated to a new angular position for another view in the same horizontal scan plane. After a desired number of views are obtained in a given horizontal scan plane, the x-ray source and detectors are moved together, relative to the patient, along a vertical translation axis to a new horizontal scan plane to obtain image information about the patient in that plane. A series of such horizontal scans may be taken and the data reconstructed to provide an image of the patient's anatomy.

The following background is useful in understanding the concepts and terminology of this art (particularly the concepts of helical source trajectory and cone beams):

In at least one known CT imaging system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In other known CT systems, the x-ray source and the detector array are rotated with a gantry within the imaging plane and around the object to be imaged so that the angle at which the x-ray beam intersects the object constantly changes. A group of x ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object.

One method for reconstructing an image from a set of projection data is referred to in the art as the filtered back-projection technique. This process converts the attenuation measurements from a scan into integers called "CT numbers" or "Hounsfield units", which can be used to control the brightness of a corresponding pixel on a cathode ray tube display.

The two-dimensional methods discussed above can reconstruct a slice of the measured object. If a volume segment needs to be reconstructed, the complete procedure can be performed slice-by-slice with a small movement of the object or of the source-detector system between each slice.

A more efficient acquisition setup for volumetric CT uses a two-dimensional detector. The rays then form a cone with its base on the detector and its apex on the source. An x-ray source naturally produces a cone of rays, so cone-beam acquisition not only increases the scanning speed, but also makes better use of the emitted rays otherwise wasted by collimation.

Modern CT scanners are rapidly moving from fan-beam towards cone-beam geometry. Current micro-CT scanners are already in cone-beam geometry. Half-scan CT algorithms are advantageous in terms of temporal resolution and are widely used in fan-beam and cone-beam geometry.

A helical source trajectory is natural for volume scanning of long objects. A continuously translated object and a rotating source-detector system yield a helical source trajectory around the object. Helical scanning has been used for many years with one-dimensional detectors and has now been extended for use with multi-row detectors with potential applications for two-dimensional detectors in the medical imaging field.

SUMMARY OF THE INVENTION

The present invention seeks to provide apparatus and technique for achieving novel source trajectories in rotating-patient CT scanning, as described more in detail hereinbelow.

There is thus provided in accordance with an embodiment of the present invention a CT scanning system including a source operable to emit a cone beam of radiation toward an object, a detector (may be stationary) operable to detect radiation emitted by the source and to produce detector values related to projections of an object attenuation, a turntable operable to rotate the object about a rotational axis (e.g., vertical), and a source mover operable to move the source so as to vary an angle between the cone beam and the rotational axis.

The source mover can move the source parallel to the rotational axis in one direction or more than one direction. Additionally or alternatively, the source mover can move the source along an arc in one direction or more than one direction.

A processor may be provided to process the detector values and reconstruct a spatial distribution related to the object attenuation. In accordance with an embodiment of the present invention the source mover is operable to move the source periodically.

There is also provided in accordance with an embodiment of the present invention a method for computed tomography including emitting a cone beam of radiation toward an object from a source, detecting radiation emitted by the source and producing detector values related to projections of an object attenuation, rotating the object about a rotational axis, and moving the source so as to vary an angle between the cone beam and the rotational axis.

In accordance with an embodiment of the present invention, the method further includes rotating the object while moving the source repeatedly so as to create a multiplicity of source displacements, each source displacement being associated with several rotation angles of the object. Rotation of the object while moving the source can create a multi-helical source trajectory, a sinusoidal source trajectory and/or a triangular source trajectory.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
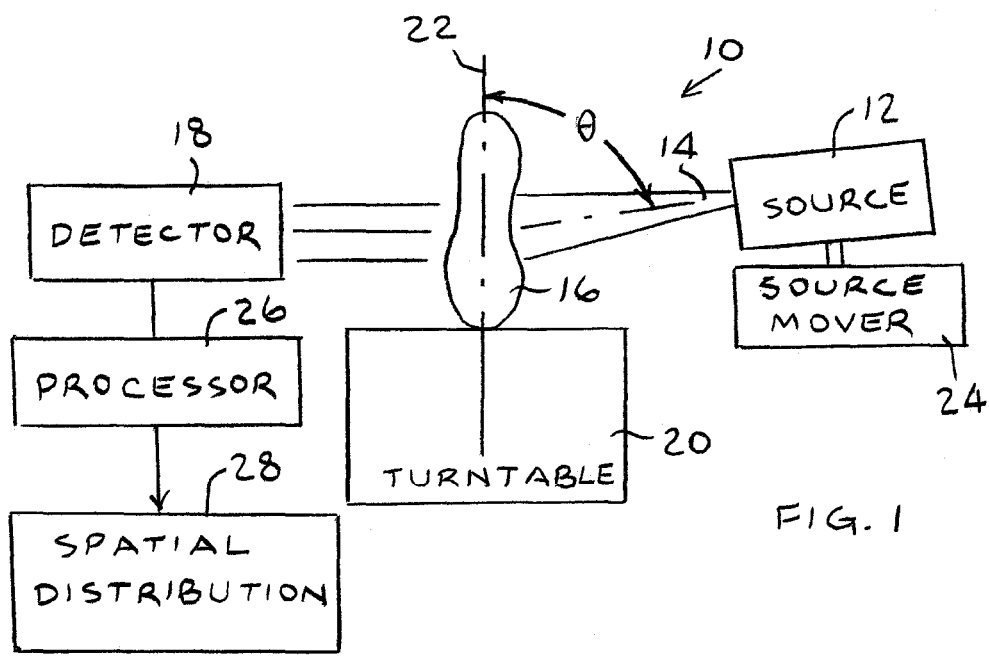
FIG. 1 is a simplified block diagram illustration of a CT scanning system, constructed and operative in accordance with an embodiment of the present invention.

Reference is now made to FIG. 1, which illustrates a CT scanning system 10, constructed and operative in accordance with a non-limiting embodiment of the present invention.

The CT scanning system 10 includes a source 12 that emits a cone beam 14 of radiation (e.g., X-ray or other radiation) toward an object 16 (e.g., a target in a patient), as is known in the art. A detector 18 detects radiation emitted by source 12 attenuated by passing through object 16. Detector 18 produces detector values related to projections of the object attenuation, as is known in the art. Detector 18 is preferably stationary.

A turntable 20 rotates object 16 about a rotational axis 22, as is known in the art. In the illustrated embodiment, rotational axis 22 is vertical, but the invention can be carried out at other angles, such as but not limited to, a horizontal axis. Such turntables are well known in the art.

A source mover 24 is operatively connected to source 12. In accordance with an embodiment of the present invention, source mover 24 moves source 12 so as to vary an angle θ between cone beam 14 and rotational axis 22. Source mover 24 can move source 12 continuously or periodically.

A processor 26 processes the detector values and reconstructs a spatial distribution 28 related to the object attenuation.

Source mover 24 is used to generate novel source trajectories, heretofore unattainable with prior art scanning systems, as is now explained with reference to FIGS. 2A-3C.

Figure 2A:
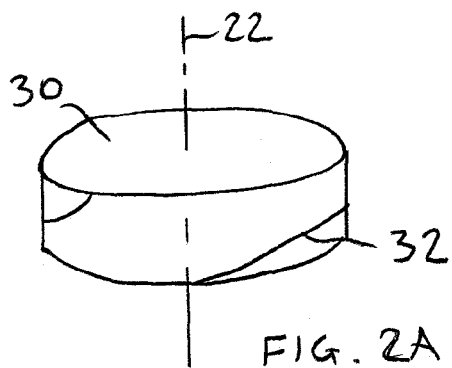
FIG. 2A is a simplified diagram of a source scanning strip.
Figure 2B:
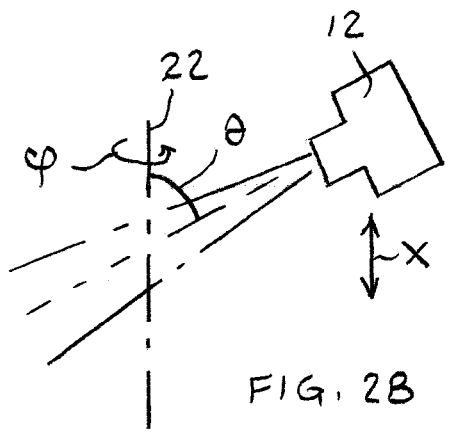
FIG. 2B is a simplified diagram of a source trajectory, showing a source, cone beam and rotation axis.

First reference is made to FIGS. 2A-2B. A source trajectory, referenced to the scanned object, can be viewed as located on a circular scanning strip 30 having a finite width, wherein the scanning strip axis is collinear with the rotational axis 22. The trajectory can be depicted in the X-φ (X-Phi) or the θ-φ (Theta-Phi) planes where φ is the rotational angle, X is the source displacement along the rotational axis and θ is the angle between the cone beam and the rotational axis. The scanning strip in the X-φ plane is defined by all the points X, φ such that: 0<X<X-max, 0<φ<φ-max where X-max and φ-max are the respective translation and rotation limits of the scanner.

As seen in FIG. 2B, the scanning strip is the "source trajectory domain". The source trajectory domain defines the geometrical limitations for possible source positions relative to the object over the scanning range.

Figure 2C:
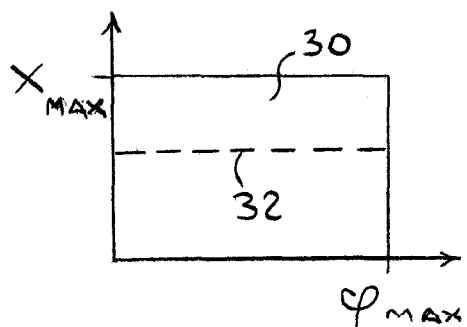
FIG. 2C is a simplified diagram of a circular source trajectory, depicted as a line parallel to the φ axis in the X-φ plane.
Figure 2D:
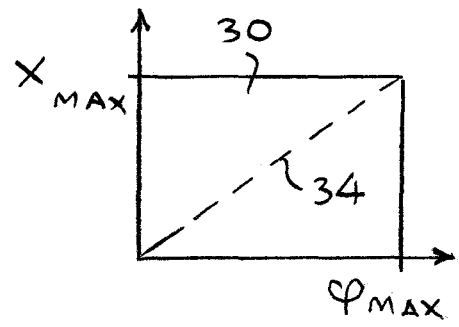
FIG. 2D is a simplified diagram of a helical trajectory, depicted as a slanted line in the X-φ plane.

A circular source trajectory 32 is typically obtained by rotating the source in a plane perpendicular to the rotational axis—depicted as a line parallel to the φ axis in the X-φ plane (FIG. 2C). A helical trajectory 34 (FIG. 2B) is typically obtained by continuously translating the object during source rotation—depicted as a slanted line in the X-φ plane (FIG. 2D).

Typically source radiation is pulsed and/or detector values are discrete. As a result, a point on the source trajectory—referred to as a view point—represents a discrete source position from which a view is taken. "Source trajectory domain coverage" refers to the amount the associated view points cover, or are distributed over, the scanning range. Using this terminology, a circular source trajectory, for example, has very low source trajectory domain coverage, since all of the view points are concentrated on a single X position in the scanning range. Such a scan is associated with increasingly reduced reconstruction accuracy away from the rotating source plane. A helical source trajectory, while having more source trajectory domain coverage than a circular one, still has low source trajectory domain coverage.

As mentioned above, source mover 24 moves source 12 so as to vary angle θ between cone beam 14 and rotational axis 22. The movement of source 12 can be coordinated with rotation of object 16. In this manner, the present invention produces source trajectories that have significantly greater source trajectory domain coverage than heretofore possible. For example, object 16 may be rotated while source 12 is moved repeatedly such that there is a multiplicity of source displacements and each one is associated with several rotation angles. Source mover 24 moves source 12 as controlled by processor 26. Source mover 24 may move source 12 parallel to rotational axis 22 in one direction or more than one direction. Additionally or alternatively, source mover 24 may move source 12 along an arc in one direction or more than one direction.

Figure 3A:
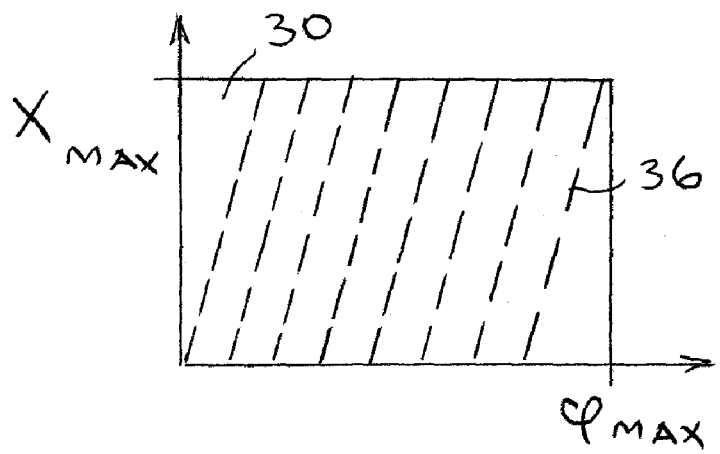
FIGS. 3A, 3B and 3C are simplified diagrams of source trajectories, in accordance with an embodiment of the present invention, having significantly greater source trajectory domain coverage than the prior art, the source trajectories being multi-helical, sinusoidal and triangular, respectively.
Figure 3B:
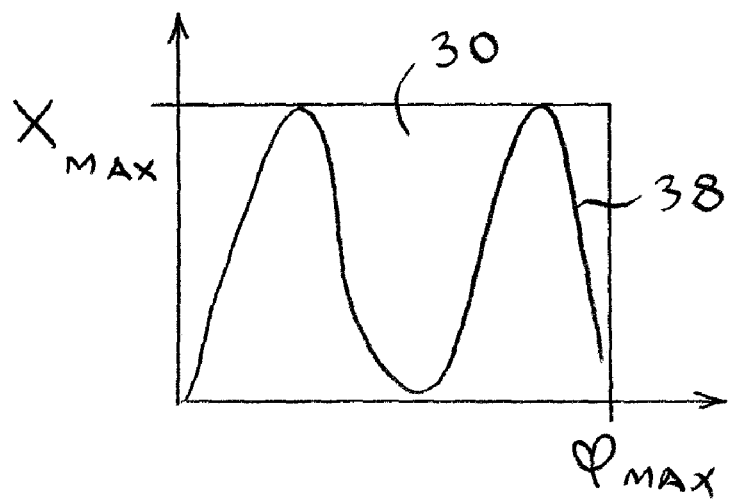
Figure 3C:
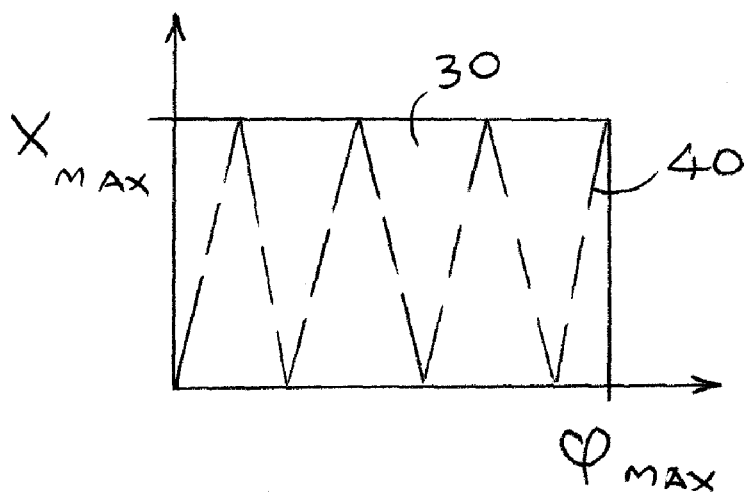

Exemplary source trajectories created by coordinated movement of source 12 and object 16 are multi-helical 36, sinusoidal 38 and triangular 40 trajectories, depicted respectively in FIGS. 3A, 3B and 3C.

The scope of the present invention includes both combinations and subcombinations of the features described hereinabove as well as modifications and variations thereof which would occur to a person of skill in the art upon reading the foregoing description and which are not in the prior art.

What is claimed is:

1. A computed tomography (CT) scanning system comprising:
   a source operable to emit a cone beam of radiation toward an object;
   a detector operable to detect radiation emitted by said source and to produce detector values related to projections of an object attenuation;
   a turntable operable to rotate the object about a rotational axis; and
   a source mover operable to move said source so as to vary an angle between said cone beam and said rotational axis, said source mover being decoupled from said detector and being operable to vary a position of said source with respect to said detector.

2. A scanning system according to claim 1, wherein said source mover moves said source parallel to said rotational axis in one direction.

3. A scanning system according to claim 1, wherein the source mover moves the source parallel to the rotational axis in more than one direction.

4. A scanning system according to claim 1, wherein the source mover moves the source along an arc in one direction.

5. A scanning system according to claim 1, wherein the source mover moves the source along an arc in more than one direction.

6. A scanning system according to claim 1, wherein the rotational axis is vertical.

7. A scanning system according to claim 1, wherein the detector is stationary.

8. A scanning system according to claim 1, further incorporating a processor operable to process said detector values and reconstruct a spatial distribution related to said object attenuation.

9. A scanning system according to claim 1, wherein said source mover is operable to move said source periodically.

* * * * *